US011697833B2

(12) United States Patent
Ozcan et al.

(10) Patent No.: US 11,697,833 B2
(45) Date of Patent: Jul. 11, 2023

(54) ANTIMICROBIAL SUSCEPTIBILITY TESTING DEVICE AND METHOD FOR USE WITH PORTABLE ELECTRONIC DEVICE

(71) Applicant: THE REGENTS OF THE UNIVERSITY OF CALIFORNIA, Oakland, CA (US)

(72) Inventors: Aydogan Ozcan, Los Angeles, CA (US); Omai Garner, Culver City, CA (US); Dino Di Carlo, Los Angeles, CA (US); Steve Wei Feng, Danville, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 939 days.

(21) Appl. No.: 16/464,681

(22) PCT Filed: Nov. 29, 2017

(86) PCT No.: PCT/US2017/063601
§ 371 (c)(1),
(2) Date: May 28, 2019

(87) PCT Pub. No.: WO2018/102346
PCT Pub. Date: Jun. 7, 2018

(65) Prior Publication Data
US 2019/0316172 A1    Oct. 17, 2019

Related U.S. Application Data

(60) Provisional application No. 62/427,689, filed on Nov. 29, 2016.

(51) Int. Cl.
*G01N 21/25* (2006.01)
*C12M 1/32* (2006.01)
(Continued)

(52) U.S. Cl.
CPC ............. *C12Q 1/18* (2013.01); *G01N 21/253* (2013.01); *G06V 10/12* (2022.01); *G06V 20/69* (2022.01);
(Continued)

(58) Field of Classification Search
None
See application file for complete search history.

(56) References Cited

U.S. PATENT DOCUMENTS 4,288,543 A    9/1981 Sielaff et al.
4,448,534 A    5/1984 Wertz et al.
(Continued)

FOREIGN PATENT DOCUMENTS

WO    WO 2016/172532 A2    10/2016
WO    WO 2016/205736 A1    12/2016

OTHER PUBLICATIONS

PCT International Search Report for PCT/US2017/063601, Applicant: The Regents of the University of California, Form PCT/ISA/210 and 220, dated Feb. 16, 2018 (4pages).
(Continued)

*Primary Examiner* — Neil N Turk
(74) *Attorney, Agent, or Firm* — Vista IP Law Group LLP

(57) ABSTRACT

A method of performing antimicrobial susceptibility testing (AST) on a sample uses a reader device that mounts on a mobile phone having a camera. A microtiter plate containing wells preloaded with the bacteria-containing sample, growth medium, and drugs of differing concentrations is loaded into the reader device. The wells are illuminated using an array of illumination sources contained in the reader device. Images of the wells are acquired with the camera of the mobile phone. In one embodiment, the images are transmitted to a separate computing device for processing to classify each well as turbid or not turbid and generating MIC values (Continued)

and a susceptibility characterization for each drug in the panel based on the turbidity classification of the array of wells. The MIC values and the susceptibility characterizations for each drug are transmitted or returned to the mobile phone for display thereon.

20 Claims, 12 Drawing Sheets

(51) Int. Cl.
| | |
|---|---|
| *C12M 1/34* | (2006.01) |
| *C12Q 1/18* | (2006.01) |
| *G06V 10/12* | (2022.01) |
| *G06V 20/69* | (2022.01) |
| *G01N 21/64* | (2006.01) |

(52) U.S. Cl.
CPC .............. *G01N 2201/0221* (2013.01); *G01N 2201/0833* (2013.01)

(56) References Cited

U.S. PATENT DOCUMENTS

| | | | |
|---|---|---|---|
| 5,861,264 | A | 1/1999 | Elrod et al. |
| 9,244,066 | B2 | 1/2016 | O'Driscoll et al. |
| 2001/0000175 | A1 | 4/2001 | Kurane et al. |
| 2003/0059187 | A1 | 3/2003 | Andrieu et al. |
| 2003/0090593 | A1* | 5/2003 | Xiong ............... H04N 5/23248 382/254 |
| 2010/0182405 | A1 | 7/2010 | Monteiro |
| 2010/0254581 | A1 | 10/2010 | Neeser et al. |
| 2012/0148141 | A1 | 6/2012 | Ozcan et al. |
| 2012/0157160 | A1 | 6/2012 | Ozcan et al. |
| 2012/0295249 | A1* | 11/2012 | Cherubini ............ G01N 35/028 435/6.12 |
| 2012/0329675 | A1* | 12/2012 | Olson ..................... C12Q 1/025 506/10 |
| 2013/0157351 | A1 | 6/2013 | Ozcan et al. |
| 2013/0203043 | A1 | 8/2013 | Ozcan et al. |
| 2013/0273528 | A1 | 10/2013 | Ehrenkranz |
| 2014/0120563 | A1 | 5/2014 | Ozcan et al. |
| 2014/0242612 | A1* | 8/2014 | Wang ..................... G01N 21/29 435/7.37 |
| 2015/0111201 | A1 | 4/2015 | Ozcan et al. |
| 2016/0160260 | A1* | 6/2016 | Marshall ................. C12Q 1/06 435/39 |
| 2016/0216208 | A1 | 7/2016 | Kim et al. |
| 2016/0327473 | A1 | 11/2016 | Ozcan et al. |
| 2018/0196193 | A1 | 7/2018 | Ozcan et al. |

OTHER PUBLICATIONS

PCT Written Opinion of the International Search Authority for PCT/US2017/063601, Applicant: The Regents of the University of California, Form PCT/ISA/237, dated Feb. 16, 2018 (10pages).
Aki, Tony J. et al., Wireless Monitoring of Liver Hemodynamics In Vivo, PLOS One, www.plosone.org, Jul. 22014, vol. 9, Issue 7, e102396.
Berg, Brandon et al., Cellphone-Based Hand-Held Microplate Reader for Point-of-Care Testing of Enzyme-Linked Immunosorbent Assays, ACSNano, www.acsnano.org, vol. 9, No. 8, 7857-7866 (2015).
Coskun, Ahmet F. et al., A personalized food allergen testing platform on a cellphone, Lab Chip, Feb. 21, 2013; 13(4): 636-640. doi:10.1039/c21241152k.
Coskun, Ahmet F. et al., Albumin testing in urine using a smartphone, Lab Chip, Nov. 7, 2013; 13(21): 4231-4238, doi:10.1039/c3lc50785h.
Coskun, Ahmet F. et al., Lensfree optofluidic plasmonic sensor for real-time and label-free monitoring of molecular binding events over a wide field-of-view, Scientific Reports, 4:6789; DOI:10.1038/srep06789.
Kadlec, Meichei Wang et al., A Cell Phone-Based Microphotometric System for Rapid Antimicrobial Susceptibility Testing, Journal of Automation, 2014, vol. 19(3) 258-266.
Laksanasopin, Tassaneewan et al., A smartphone dongle for diagnosis of infectious diseases at the point of care, www.ScienceTranslationalMedicine.org, Feb. 4, 2015, vol. 7, Issue 273, 273re1.
Lee, Seoho et al., NutriPhone: a mobile platform for low-cost point-of-care quantification of vitamin B12 concentrations, Scientific Reports, 6:28237; DOI:10.1038/srep28237, www.nature.com/scientificreports (Jun. 15, 2016).
Ludwig, Susan K.J. et al., Calling Biomarkers in Milk Using a Protein Microarray on Your Smartphone, https://doi.org/10.1371/journal.pone.0134360 (Aug. 26, 2015).
Mcgeough, Cathy M. et al., Camera Phone-Based Quantitative Analysis of C-Reactive Protein ELISA, IEEE Transactions on Biomedical Circuits and Systems (6pages) (2013).
Mudanyali, Onur et al., Integrated Rapid-Diagnostic-Test Reader Platform on a Cellphone, Lab Chip, Aug. 7, 2012; 12(15): 2678-2686. doi:10.1039/c21c40235a.
Ozcan, Aydogan, Mobile phones democratize and cultivate next-generation imaging, diagnostics and measurement tools, Lab Chip (2014); DOI: 10.1039/c4lc00010b.
Tseng, Derek et al., Lensfree microscopy on a cellphone, Lab Chip, Jul. 21, 2010; 10(14): 1787-1792, doi:10.1039/c003477k.
Venkatesh, A.G. et al., Smartphone-based colorimetric readers for cost-effective in vitro diagnostics, MikroSystemTechnik Kongress 2015, 26-28, (Oct. 2015).
Wei, Qingshan et al., Detection and Spatial Mapping of Mercury Contamination in Water Samples Using a Smart-Phone, ACSNano, www.acsnano.org., vol. 8, No. 2, 1121-1129 (2014).
Wei, Qingshan et al., Imaging and Sizing of Single DNA Molecules on a Mobile Phone, ACSNano, www.acsnano.org., vol. 8, No. 12, 12725-12733 (2014).
Zhu, Hongying et al., Cost-effective and compact wide-field fluorescent imaging on a cell-phone, Lab Chip, Jan. 21, 2011; 11(2):315-322. doi:10.1039/c01c00358a.
Zhu, Hongying et al., Quantom dot enabled detection of *Escherichia coli* using a cell-phone, Analyst. Jun. 7, 2012; 137(11):2541-2544. doi:10.1039/c2an35071h.
Zhu, Hongying et al., Optofluidic Fluorescent Imaging Cytometry on a Cell Phone, Anal Chem. Sep. 1, 2011; 83(17): 6641-6647. doi:10.1021/ac201587a.
PCT International Preliminary Report on Patentability (Chapter I of the Patent Cooperation Treaty) for PCT/US2017/063601, Applicant: The Regents of the University of California, Form PCT/IB/326 and 373, dated Jun. 13, 2019 (12 pages).

* cited by examiner

FIG. 8A

Antimicrobial Susceptibility Test (AST) Reader

New Test

History

FIG. 8B

AST Reader

Select Images:
Dim Image
Select Image
Image Upload
IMG

Select Images:
Moderate Image
Select Image
Image Upload
IMG

Select Images:
Bright Image
Select Image
Image Upload
IMG

Next

FIG. 8C

AST Reader

Select Bacteria Group and Test Type:
Gram-Neg  Gram-Pos search for bacterium Klebsiella pneumoniae
Klebsiella oxytoca
Klebsiella oxytoca #2

Submit

FIG. 8D

AST History

- 2016/04/10 7:52pm Kleb Pneu
- 2016/04/09 4:30pm Kleb Pneu
- 2016/04/09 4:44pm Kleb Pneu
- 2016/04/08 12:25pm Kleb Pneu
- 2016/04/08 1:28pm Kleb Pneu Main Menu

FIG. 8E

AST Reader
susceptibility turbidity

| | MIC | Susceptibility |
|---|---|---|
| CONTROL | --- | POS |
| AM | >32 | Resistant |
| A/S | <=8 | Susceptible |
| CPM | <=0.5 | Susceptible |
| MPM | <=0.25 | Susceptible |
| GM | <=0.5 | Susceptible |
| TB | <0.5 | Susceptible |
| AK | 1 | Susceptible |
| CZ | 2 | Susceptible |
| CTRX | <=0.5 | Susceptible |
| CAZ | <=0.5 | Susceptible |

Upload Time: 4/10/16 7:52 PM

Main Menu

FIG. 8F

AST Reader
susceptibility turbidity

Upload Time: 4/10/16 7:52 PM

Main Menu

US 11,697,833 B2

ANTIMICROBIAL SUSCEPTIBILITY TESTING DEVICE AND METHOD FOR USE WITH PORTABLE ELECTRONIC DEVICE

RELATED APPLICATION

This Application is a U.S. National Stage filing under 35 U.S.C. § 371 of International Application No. PCT/US2017/063601, filed Nov. 29, 2017, which claims priority to U.S. Provisional Patent Application No. 62/427,689 filed on Nov. 29, 2016, which are hereby incorporated by reference in its entirety. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant No. 1332275, awarded by the National Science Foundation. The government has certain rights in the invention.

TECHNICAL FIELD

The technical field generally relates to devices and methods that are used for antimicrobial susceptibility testing. More particularly, the invention relates to a modular reader device that is used together with a portable electronic device such as mobile phone to automatically determine drug-specific minimum inhibitory concentration (MIC) values and the corresponding susceptibility.

BACKGROUND

The increasing prevalence of antimicrobial resistance represents a severe threat to global health and is becoming more common with respect to bacterial pathogens responsible for high mortality diseases including pneumonia, diarrheal disease, and sepsis. Part of the global challenge in combating these organisms is that routine antimicrobial susceptibility testing (AST) is not often performed due to technological challenges, high costs, and lack of professional training, which greatly contributes to high mortality and the global spread of multi-drug resistant organisms. The goals of antimicrobial susceptibility testing include the detection of possible drug resistance and assurance of susceptibility to drugs of choice for each particular infection.

The current gold standard for antimicrobial susceptibility testing is the broth microdilution method. This procedure involves preparing two-fold dilutions of antibiotics in a liquid growth medium that is dispensed in a 96-well microtiter plate (MTP), with plates typically prepared for standard bacterial groups (e.g., Gram-negative or Gram-positive). The antibiotic-containing wells are inoculated with a standardized bacterial suspension with bacteria isolated from a patient. Following overnight incubation, the plates are placed in a plate reader that includes mirror that enables the user to view the bottom of the array of wells. The wells are thus examined by a trained expert for visible growth as evidenced by turbidity (i.e., turbidity indicates growth of bacteria).

The lowest concentration of antibiotic that prevented bacterial growth represents the minimum inhibitory concentration (MIC). This is a quantitative result that allows tracking of resistance. The MIC value is then interpreted using a pre-existing table of values that relate to the proven clinical efficacy of each antibiotic for various bacterial species. An interpretive criterion (e.g., susceptible, intermediate or indeterminate, and resistant) is assigned to each bacteria/drug combination in order to guide the physician in treatment decisions. These interpretive criteria have been established by both the U.S. Food and Drug Administration (FDA) and the Clinical Laboratory Standards Institute (CLSI) using data from animal studies, microbiological studies, and clinical efficacy data. A "susceptible" result indicates that the patient's organism should respond to therapy, while a "resistant" organism will not be inhibited by the concentrations of antibiotic achieved with normal dosages used for that drug. An "indeterminate" or "intermediate" result indicates that antimicrobial activity is associated with an indeterminate or uncertain therapeutic effect. In this regard, a physician can use the MIC result and the resulting clinical interpretation to decide whether a particular antibiotic should be used for a particular patient.

An important part of the challenge for this gold standard testing is that a high level of clinical microbiology expertise and tedious examination of the well plate is required to accurately read the turbidity from the MTP and to establish the interpretive criteria necessary for treatment. An additional challenge is that the data collected in clinical microbiology laboratories are not easily available for epidemiological studies, and are not available at all in regions of the world where antimicrobial susceptibility testing is not regularly performed.

SUMMARY

An antimicrobial susceptibility testing (AST) system is disclosed herein that is usable with portable electronic devices such as mobile phones, tablet PCs, and the like that can serve as a cost-effective, hand-held, and automated turbidity reader for rapid quantification and analysis of micro-well susceptibility results. In one embodiment, the AST system is paired with a Smartphone and uses a portable opto-mechanical modular attachment that is used in conjunction with the Smartphone to illuminate the test plate and obtain images using the camera functionality of the Smartphone. The system includes a data processing computing device or computer (e.g., a laptop, PC, tablet PC, Smartphone, or remote server) that is in communication with a software application running on the Smartphone that includes an intuitive, interactive graphical user interface (GUI). The AST system uses a conventional MTP that holds patient or subject samples as well as antimicrobial drugs at varying dilutions.

After inserting an antimicrobial susceptibility test plate into the modular opto-mechanical attachment, the camera of the Smartphone is used by the software application to capture the transmitted light from each well of the MTP at multiple exposures. The software application then uploads or transfers these images to the computing device running image processing software to automatically quantify well turbidity based on the transmitted light. By selecting the drug target type of the treated plate (e.g., Gram-negative or Gram-positive) and the microbe of interest, the server then determines the drug-specific MIC and corresponding interpretive criteria and returns the results to the user through the same software application. Typically, results will be returned to the user within about one (1) minute or less.

Experiments were conducted to demonstrate the mobile AST reader's ability to automatically determine drug-specific MIC and corresponding drug resistance through a comprehensive clinical evaluation performed at the UCLA Clinical Microbiology Laboratory using plates containing seventeen (17) different antibiotics targeted for Gram-negative bacteria and tested on patient isolates of *Klebsiella pneumoniae*. This species of bacteria can exhibit highly resistant antimicrobial profiles and contain members of the Carbapenem resistant Enterobacteriaceae (CRE), with a very high mortality rate in multiple disease states including sepsis and pneumonia. CRE have complicated antimicrobial resistance profiles and represent a significant challenge to global health. The mobile AST reader's performance exceeded the FDA-defined criteria for susceptibility testing, with an MIC agreement of >95% with no very major errors (i.e., resistant microbes misdiagnosed as susceptible), 0.16% major errors (i.e., susceptible microbes misdiagnosed as resistant), and 0.65% minor errors (i.e., indeterminate/susceptible dose dependent-related misdiagnoses).

In one embodiment of the invention, a method of performing antimicrobial susceptibility testing (AST) uses an opto-mechanical reader device configured to mount on a mobile phone including camera functionality includes securing the opto-mechanical reader device to the mobile phone. An optically transparent plate containing an array of wells loaded with a bacteria-containing sample, growth medium, and a panel of drugs of differing concentrations is loaded into the opto-mechanical reader device. The optically transparent plate could also be loaded into the opto-mechanical reader device prior to being secured to the opto-mechanical reader device. The wells in the optically transparent plate are illuminated using an array of illumination sources contained in the opto-mechanical reader device. One or more images of the wells are acquired with the camera of the mobile phone, wherein the one or more images represent light transmittance through the wells. The image or images obtained with the camera are, in one embodiment, transmitted to separate computing device that is used for image processing. In another embodiment, the mobile phone itself is used as the computing device for imaging processing. Regardless of the computing device, the one or more images are processed by image processing software executed by the computing device to classify each well as turbid or not turbid and generating MIC values and a susceptibility characterization for each drug in the panel based on the turbidity classification of the array of wells. The MIC values and the susceptibility characterizations for each drug in the panel are, in some embodiments, transmitted to the mobile phone or another computing device for display thereon. Alternatively, the mobile phone may itself generate MIC values and a susceptibility characterizations for display directly on the screen or display of the mobile phone without the need for transmission of this information.

In another embodiment, a method of performing antimicrobial susceptibility testing (AST) using a opto-mechanical reader device configured to mount on a portable electronic device includes the operations of securing the opto-mechanical reader device to the portable electronic device. The opto-mechanical reader device is loaded with an optically transparent plate containing an array of wells loaded with a bacteria-containing sample, growth medium, and a panel of drugs of differing concentrations. The optically transparent plate could also be loaded into the opto-mechanical reader device prior to being secured to the opto-mechanical reader device. The wells in the optically transparent plate are illuminated using an array of illumination sources contained in the opto-mechanical reader device. One or more images of the wells are obtained with the camera of the portable electronic device (e.g., mobile phone), wherein the one or more images represent light transmittance through the wells. The one or more images that contain light transmittance data are then subject to image processing to classify each well as turbid or not turbid and generating MIC values and a susceptibility characterization for each drug in the panel based on the turbidity classification of the array of wells. The image processing operation may take place on the portable electronic device or they may be transmitted to another computer device for processing. The MIC values and the susceptibility characterizations for each drug in the panel are then transferred back to the portable electronic device (in the event another computing device performs image processing) and displayed on the display of the portable electronic device to the user.

In one embodiment, a method of performing antimicrobial susceptibility testing (AST) on a sample containing bacteria uses an opto-mechanical reader device configured to mount on a portable electronic device having a camera. The mechanical reader device is secured to the portable electronic device. An optically transparent plate having an array of wells containing a bacteria-containing sample, growth medium, and a panel of drugs of differing concentrations is loaded into the opto-mechanical reader device (the plate may also be loaded prior to securing the reader device to the portable electronic device). The wells in the optically transparent plate are illuminated using an array of illumination sources contained in the opto-mechanical reader device. One or more images of the wells in the array are acquired with the camera of the portable electronic device, wherein the one or more images represent light transmittance through the wells in the array. These images are captured using an array of optical fibers that transmit light to the camera of the portable electronic device. The one or more acquired images are then processed with image processing software executed by at least one processor to classify each well as turbid or not turbid and generating MIC values and a susceptibility characterization for each drug in the panel based on the turbidity classification of the array of wells. This image processing software may reside on the portable electronic device or on a separate computing device that is in communication with the portable electronic device (e.g., through a wired or wireless connection). The MIC values and the susceptibility characterizations for each drug in the panel can then be displayed on the portable electronic device or other computing device.

In another embodiment, a method of performing antimicrobial susceptibility testing (AST) on a sample containing bacteria uses an opto-mechanical reader device configured to mount on a mobile phone having a camera. The opto-mechanical reader device is secured to the mobile phone. An optically transparent plate having an array of wells containing the bacteria-containing sample, growth medium, and a panel of drugs of differing concentrations is loaded into the opto-mechanical reader device (the plate may also be loaded prior to securing the reader device to the mobile phone). The wells in the optically transparent plate are illuminated using an array of illumination sources contained in the opto-mechanical reader device. One or more images of the wells are acquired with the camera of the mobile phone, wherein the one or more images represent light transmittance through the wells. The one or more images are transmitted to a separate computing device. The one or more transmitted images are then processed with image processing software executed by at least one processor in the separate computing device to classify each well as turbid or not turbid and generating MIC values and a susceptibility characterization for each drug in the panel based on the turbidity classification of the array of wells. The MIC values and the susceptibility characterizations for each drug in the panel are then transmitted from the separate computing device to the mobile phone or another computing device for display thereon.

In another embodiment, a method of performing antimicrobial susceptibility testing (AST) on a bacteria-containing sample using an opto-mechanical reader device configured to mount on a mobile phone. The opto-mechanical reader device is secured to the mobile phone. The opto-mechanical reader device is loaded with an optically transparent plate having an array of wells containing the bacteria-containing sample, growth medium, and a panel of drugs of differing concentrations. The wells in the optically transparent plate are illuminated using an array of illumination sources contained in the opto-mechanical reader device. One or more images of the wells are acquired with the camera of the mobile phone, wherein the one or more images represent light transmittance through the wells. The one or more transmitted images are processed using software or an application in the mobile phone to classify each well as turbid or not turbid and generating MIC values and a susceptibility characterization for each drug in the panel based on the turbidity classification of the array of wells. The MIC values and the susceptibility characterizations for each drug in the panel are displayed on the mobile phone.

In another embodiment, a system for performing antimicrobial susceptibility testing (AST) on a bacteria-containing sample includes a portable electronic device having a camera. This may include, for example, a mobile phone, tablet PC, webcam, and digital camera. The system uses an opto-mechanical reader device that is configured to mount on the portable electronic device and includes a slot or opening dimensioned to receive an optically transparent plate having an array of wells containing the bacteria-containing sample, growth medium, and a panel of drugs of differing concentrations. The opto-mechanical reader device has a plurality of illumination sources contained therein and configured to illuminate the array of wells, the opto-mechanical reader device further comprising a plurality of optical fibers, each fiber arranged to transmit light from one of the wells to the camera to generate one or more images. Thus, the fibers transmit light passing through each well to the camera. The intensity of light passing through the wells varies depending on whether bacteria grow within the wells. The system includes a computing device having image processing software contained therein (e.g., image processing software or an application) that is executable by at least one processor to process the one or more images and classify each well as turbid or not turbid and generating MIC values and a susceptibility characterization for each drug in the panel based on the turbidity classification of the array of wells.

BRIEF DESCRIPTION OF THE DRAWINGS

FIGS. 8A-8F illustrate different "pages" or screens of a graphical user interface (GUI) of a software application executed on the mobile phone (or other computing device) and used to view MIC and susceptibility results.

DETAILED DESCRIPTION OF ILLUSTRATED EMBODIMENTS

FIGS. 1A-1C, 2, and 4 illustrates an embodiment of the antimicrobial susceptibility testing (AST plate) reader 10 for use with a portable electronic device 100 (illustrated in FIGS. 1B, 1C, 1D, 1E, 2, and 4) having a camera 102 (best seen in FIG. 1E) therein. In one embodiment, the portable electronic device 100 is a mobile phone or cell phone (e.g., Smartphone) although the portable electronic device 100 may also include other portable electronic devices with a camera 102. These include, for example, an iPad®, tablet PC, webcam, and digital camera. The AST plate reader 10 is, in one particular embodiment, portable and is hand-held (either with one or both hands depending on portable electronic device 100 being used). In one aspect of the invention, the portable electronic device 100 also has wireless functionality such that images and data may be transferred to a computing device 108 (e.g., server, PC, tablet PC, or laptop) as explained herein. Wireless functionality may occur over a Wi-Fi network that is connected to the Internet. Alternatively, wireless functionality may be provided on a mobile phone network. Bluetooth® wireless transfer or other nearfield communication protocols may also be used to transfer data and images to a physically nearby yet separate remote computer. A wired connection may also be used to transfer data between a local computer such as a PC or laptop.

Figure 2:
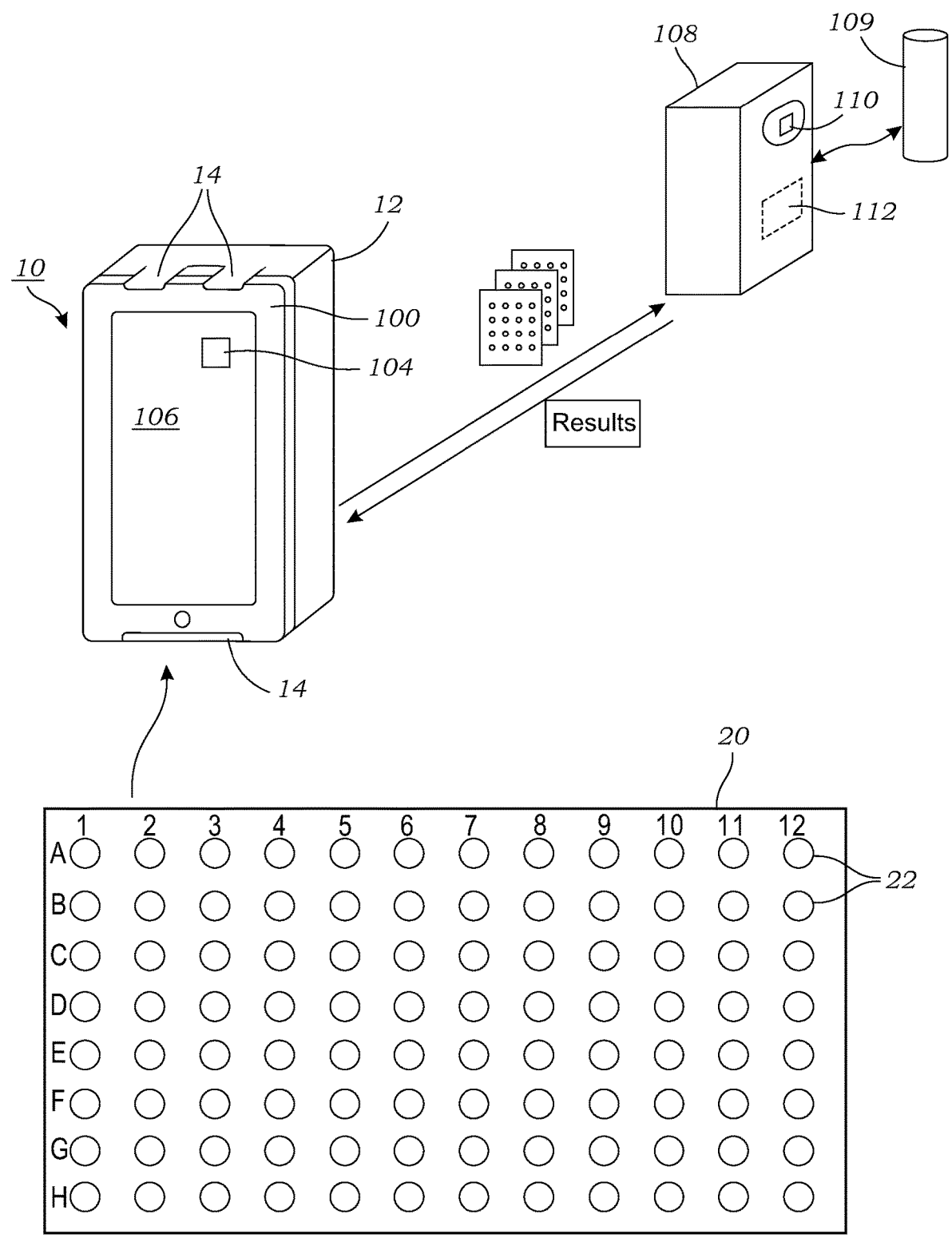
FIG. 2 illustrates a system level diagram illustrating how the mobile phone and AST plate reader device communicates with a computing device whereby turbidity, MIC, and MIC characterizations of images obtained using the AST plate reader are processed. Results can then be returned to the mobile phone.
Figure 4:
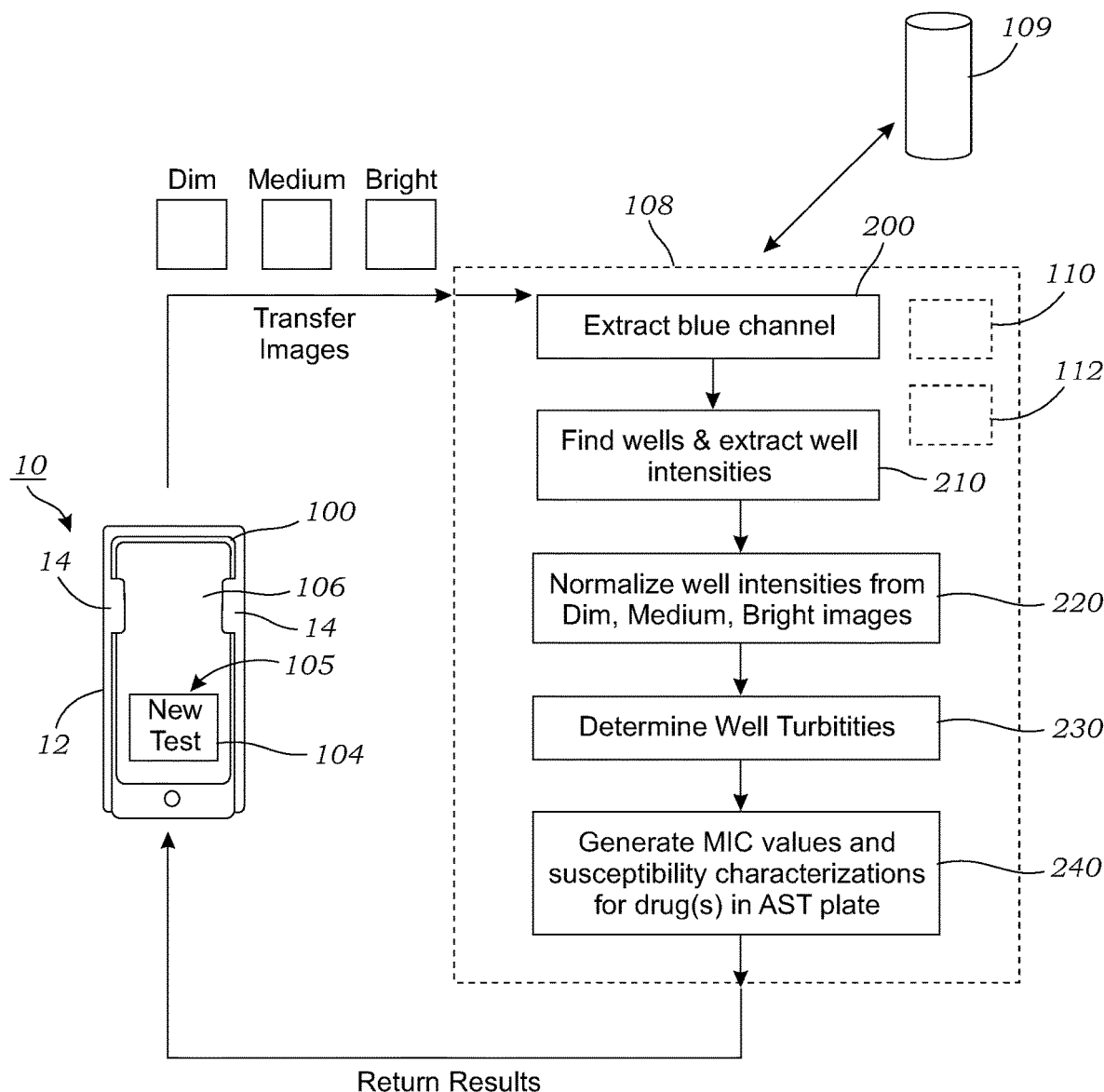
FIG. 4 illustrates a schematic overview of reader-computing device (e.g., client-server) communication and image analysis used in the AST plate reader. Using a custom-developed mobile phone software application, three images of the AST plate taken at different exposure times are uploaded to the computing device. The automated algorithm finds the wells using the blue channel of the brightest exposure image and extracts the average well intensity. The well intensities for the three exposures are then combined to maximize the dynamic range of the measured intensities and normalized respective to the maximum transmittance as obtained from blank plate control wells. These well intensities are then thresholded based off a database of uploaded plates (i.e., control plates) and processed to determine each drug's minimum inhibitory concentration and susceptibility. These results are stored on the server along with the uploaded plate images, and also returned to the client application to be shown to the user.

In one embodiment of the invention, the portable electronic device 100 includes software or an application 104 (seen in FIG. D, FIG. 2, and FIG. 4) that runs on the portable electronic device 100. A user may interface with the application 104 using a graphical user interface (GUI) 105 as illustrated in FIG. 4 and FIGS. 8A-8F that is displayed on the display 106 of the portable electronic device 100. FIGS. 8A-8F illustrate an example of a GUI interface 105 that is displayed on the display 106 and is utilized by the user to interface with the software program or application 104. The application 104 may be used by the user to run the AST test, transfer data and image files to a separate computing device 108 (which is optional in some embodiments), receive data from the computing device 108 (which is optional in some embodiments). In other embodiments as described herein, image processing and data analysis may occur exclusively on the portable electronic device 100 in which case there is no need to transfer/receive data and images to a separate computing device 108. Of course, this option may require additional computational resources that might not be available on all portable electronic devices 100. Thus, the system and method described herein further contemplates embodiments where images that are obtained using the portable electronic device 100 are transferred to a computing device 108 as illustrated in FIGS. 2 and 4.

The computing device 108 may reside locally near the portable electronic device 100 (e.g., local computer) and transfer may be accomplished over a wired or wireless connection. Alternatively, the computing device 108 may be remotely located away from the portable electronic device 100. For example, the computing device 108 may be a server that is accessed via a wireless connection formed between the portable electronic device 100 and the server. As seen in FIGS. 2 and 4, the computing device 108 includes one or more processors 110 that are used to execute software 112 for image processing and data analysis. For example, in one illustrative embodiment, the computing device 108 is a server that runs on Python and the image processing and data analysis is implemented using MATLAB® based software routines. Of course, it should be understood that the methods described herein may be employed on any number of software platforms. The computing device 108 may also include other types of computing devices such as a personal computer, tablet PC, laptop, Smartphone, or other mobile computing device.

Figure 1A:
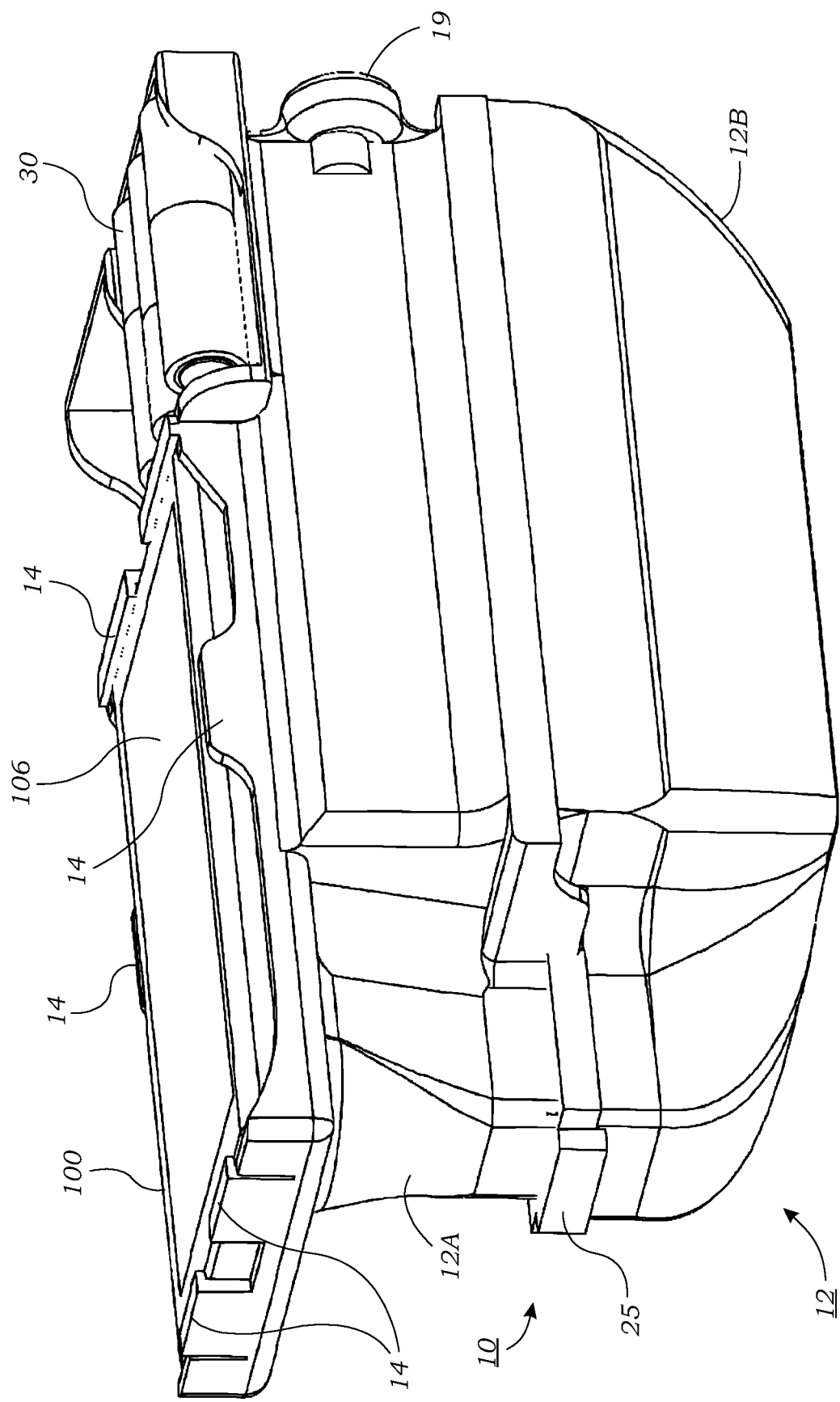
FIG. 1A illustrates a perspective view of a hand-held AST plate reader according to one embodiment of the invention
Figure 1B:
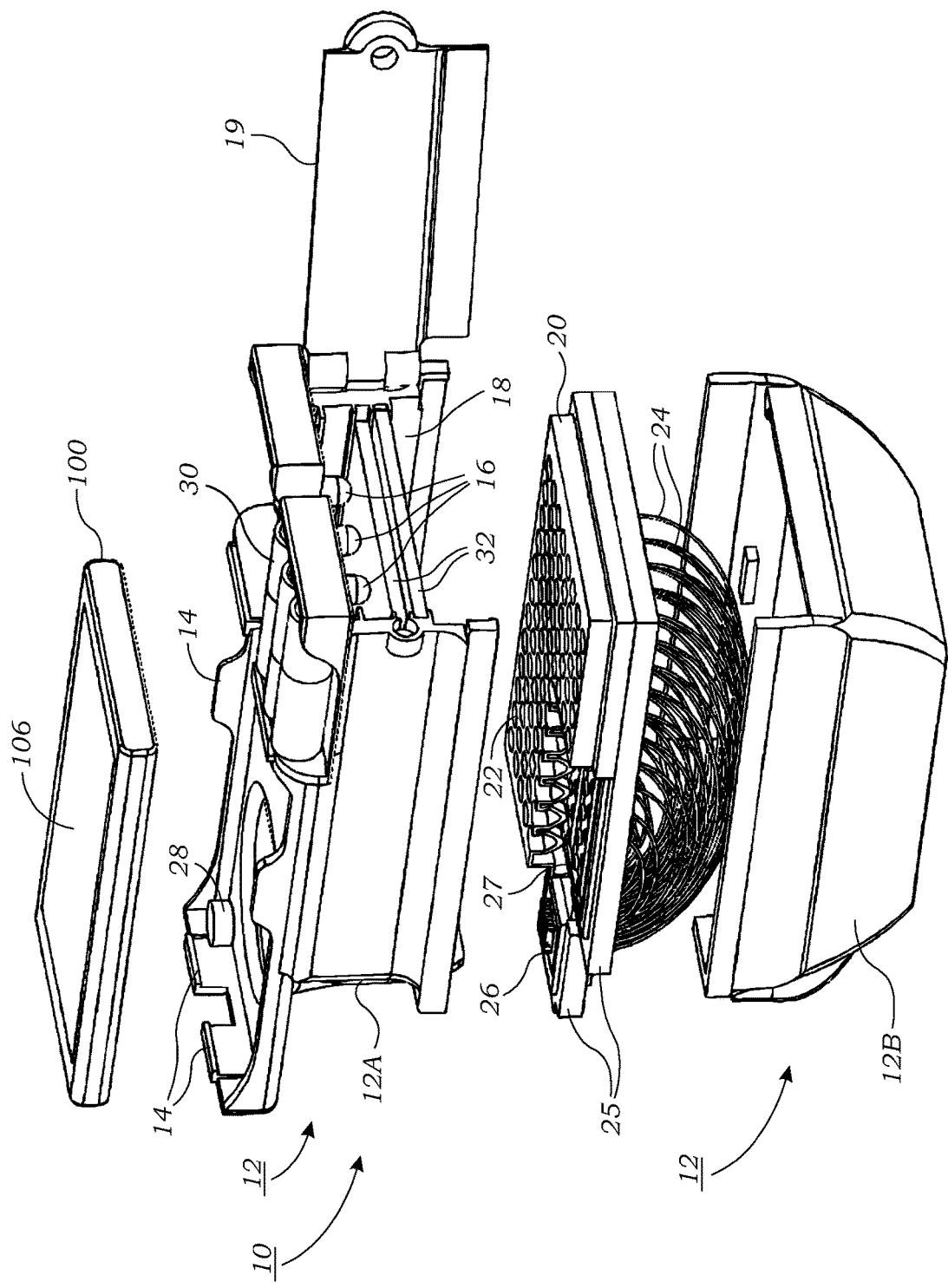
FIG. 1B illustrates an exploded, perspective view of the hand-held AST plate reader of FIG. 1A.
Figure 1C:
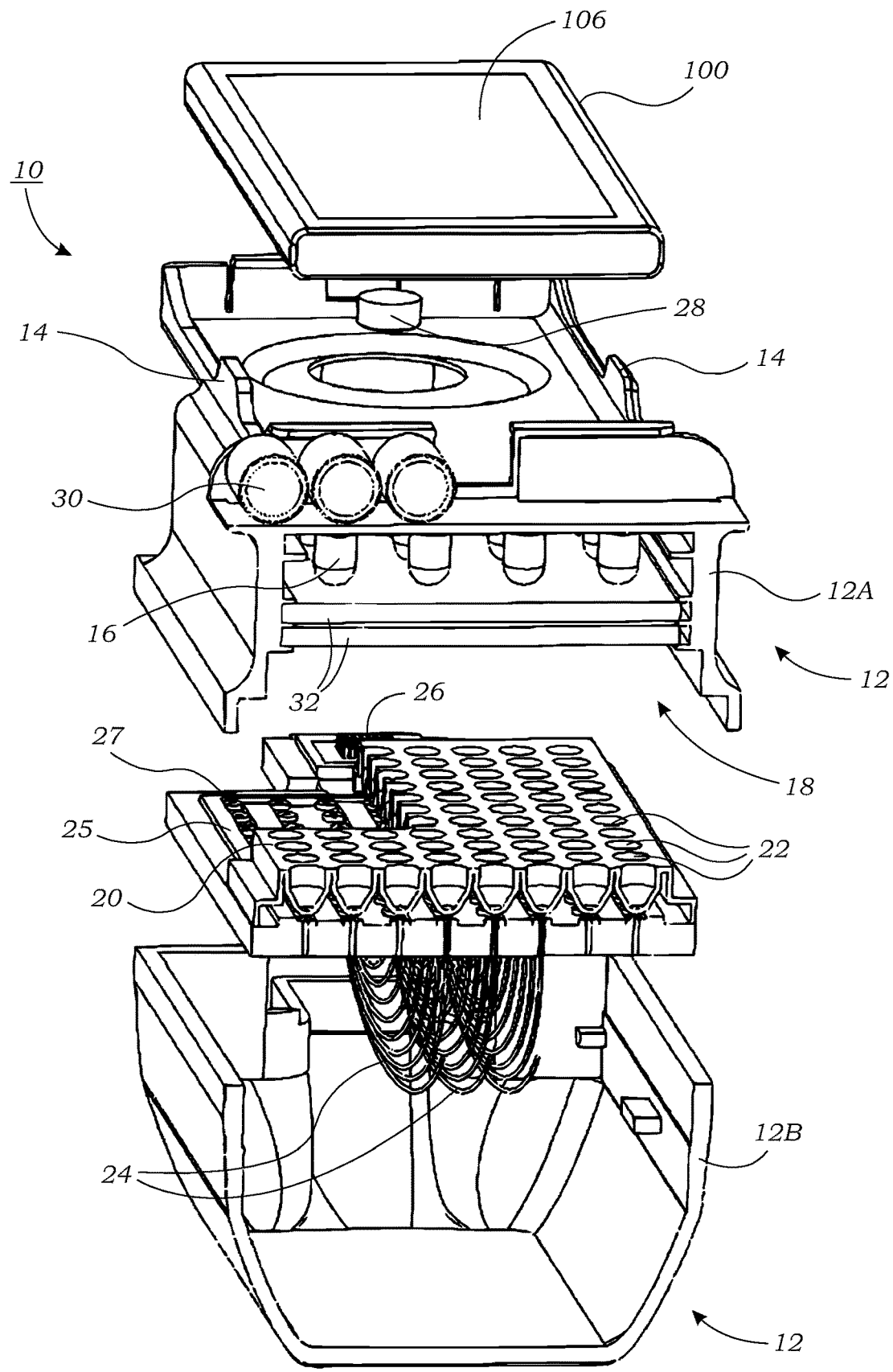
FIG. 1C illustrates a cross-sectional, exploded perspective view of the hand-held AST plate reader of FIGS. 1A and 1B.

As seen in FIGS. 1A-1C, 2, and 4, the AST plate reader 10 includes an opto-mechanical attachment 12 that is configured to attach/detach to the portable electronic device 100. As seen in the exploded views of FIGS. 1B and 1C, the opto-mechanical attachment 12 may be formed from multiple parts. An upper part 12A, which is secured to the portable electronic device 100, contains the power source 30 and illumination sources 16 (FIGS. 1B and 1C). Optical diffusers 32 are positioned adjacent the illumination sources 16 to aid in diffusing the light emitted from the plurality of illumination sources 16. A slot or opening 18 is formed on one side of the optical diffusers 32 that is used to receive an optically transparent AST plate 20. The optically transparent AST plate 20 may be a conventional 96 well plate as are well known to those skilled in the art.

Figures 1D, 1E:
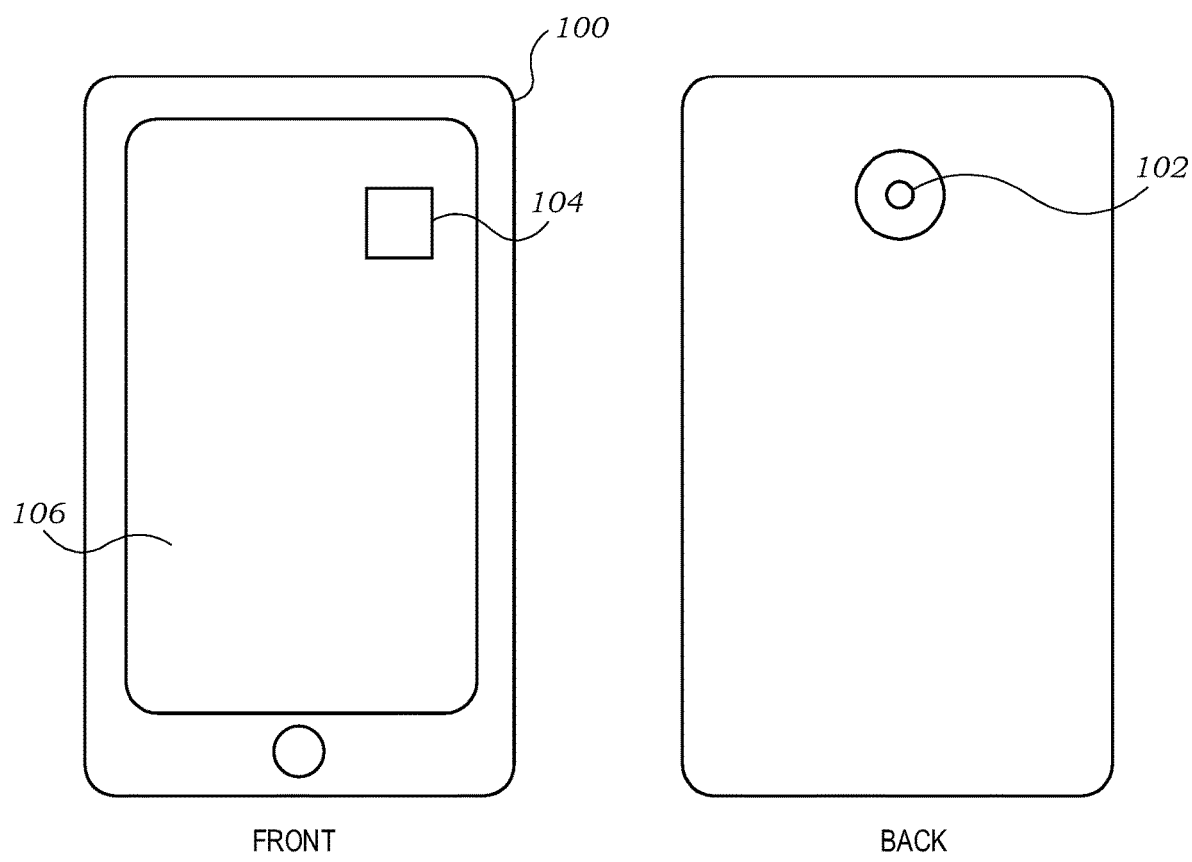
FIG. 1D illustrates a front view of a portable electronic device (e.g., mobile phone) according to one embodiment.
FIG. 1E illustrates a back view of a portable electronic device (e.g., mobile phone) according to one embodiment. The portable electronic device includes a camera therein.

A lower part 12B is secured to the upper part 12A and covers the lower portion of a base plate 25 and provides space for the optical fibers described herein. The upper part 12A of the opto-mechanical 12 attachment may include one or more fasteners 14 such as tabs, clips, or the like that are used to removably fasten the opto-mechanical attachment 12 to the portable electronic device 100. As seen in FIGS. 1A-1C, the opto-mechanical attachment 12 is secured to the "back" side of the portable electronic device 100 (e.g., the back of the mobile phone that has the camera 102 located on the back as seen in FIG. 1E) leaving the display 106 unobstructed so that it can be used while the opto-mechanical attachment 12 is secured thereto. The opto-mechanical attachment 12 may be made from a number of different materials although polymer based materials provide for a sturdy yet lightweight construction. The opto-mechanical attachment 12 may be designed specifically to fit a particular make or model of portable electronic device 100. Alternatively, the opto-mechanical attachment 12 may include one or more adjustable fasteners 14 or the like such that a single version of the opto-mechanical attachment 12 may be used on different makes and models of portable electronic devices 100 which have different sizes and different locations of the camera 102.

The opto-mechanical attachment 12 defines a housing that contains the various components required for the illumination of the optically transparent AST plate 20 as well as the optical components required to transmit collected light to the camera 102 of the portable electronic device 100. The overall dimensions of the opto-mechanical attachment 12 are, in one illustrative embodiment, 195 mm×98 mm×100 mm. The opto-mechanical attachment 12 as used in the experiments described herein weighed ~0.62 kg, which is very light and lends itself to portable use. All the components of the opto-mechanical attachment 12 used in the experiments described herein cost ~$100 USD in total, even at very low production volumes. An automated AST platform, on the other hand, typically costs significantly more (e.g., ~$30,000) and would be much larger and heavier compared to the hand-held reader 10 described herein.

The AST plate reader 10 includes a plurality of illumination sources 16 that used to illuminate the wells 22 contained in the optically transparent AST plate 20 as explained herein. In one preferred embodiment, the plurality of illumination sources 16 are configured as an array of illumination sources. For example, for the experiments described herein, the plurality of illumination sources 16 was an array of twenty-four (24) blue light emitting diodes (LEDs) (e.g., having center wavelength located between ~400 nm and ~600 nm). Alternatively, laser diodes may be used. While blue-colored light was emitted it should be appreciated that other colors could be used. The AST plate reader 10 includes a slot or opening 18 that is dimensioned to accommodate an optically transparent AST plate 20 that contains an array of wells 22 contained therein. The slot or opening 18 may be exposed or closed using a hinged door 19 (FIGS. 1A and 1B) that is opened to insert or remove the optically transparent AST plate 20. The door 19 is closed when imaging is performed. The optically transparent AST plate 20 contains an array of wells 22 that are typically arranged in rows and columns. For example, a common configuration is the so-called 96 well plate which contains an 8×12 array of wells 22 as seen in FIG. 2. Commercially available 96 well plates are readily available and, in some embodiments, may be used with the AST plate reader 10 described herein. In other embodiments, the AST plate 20 may be proprietary or custom designed to fit within the slot/opening 18. The slot or opening 18 is dimensioned to have a depth and width to accommodate the optically transparent AST plate 20 with the array of wells 22. The slot or opening 18 preferably is dimensioned so that, when fully inserted into the opto-mechanical attachment 12, each well 22 is positioned adjacent to a separate optical fiber that is used to transmit light passing through each well 22 as explained below.

Each well 22 is sized to hold a sample therein. For AST testing, the wells 22 are pre-prepared or pre-loaded with a liquid growth medium along with dilutions of different antibiotics (e.g., two-fold dilutions). The bacteria-containing sample is added to the wells 22 and the AST plate 20 is allowed to incubate for a period of time to allow the bacteria to grow and divide. Generally, the AST plate 20 is allowed about twenty-four (24) hours of incubation time prior to analysis. However, in some embodiments, the AST plate 20 may be read using the AST plate reader 10 earlier than this time period. A particular advantage of this automated platform is its ability to detect turbidity early in the bacteria growth phase and before the typical incubation times used in manual examinations. Thus, the AST plate 20 may analyzed before the typical twenty-four (24) hour incubation time period.

As seen in FIGS. 1B and 1C, the housing of the opto-mechanical attachment 12 includes a plurality of optical fibers 24. Each optical fiber 24 of the plurality includes two opposing ends. A first end of each optical fiber 24 is secured in position such that when the optically transparent AST plate 20 is inserted into the slot or opening 18 of the AST plate reader 10, the first end is located at or adjacent to one of the wells 22 located in the optically transparent AST plate 20 (the end of the optical fiber 24 should preferably be centered with respect to each well 22 of the optically transparent AST plate 20). In one aspect of the invention, the opto-mechanical attachment 12 includes a base plate 25 that is used to secure the first ends of the optical fibers 24. The base plate 25 has a plurality of apertures 27 formed therein that receive the first ends of the optical fibers 24. The optical fibers 24 are secured in the apertures 27 and collectively define an input array of optical fibers. The optical fibers 24 can be secured to the base plate 25 using glue, adhesive, or other bonding material. While FIG. 1C illustrates a single aperture 27 associated with each well 22 that contains a single fiber 24, there could be multiple apertures 27 associated with a single well 22 such that multiple fibers 24 carry the light from a single well 22 (or multiple fibers 24 could even be secured in a single aperture 27 to achieve the same result). The location of the apertures 27 in the base plate 25 is arranged to correspond to the location of the wells 22 in the optically transparent AST plate 20 as seen in FIG. 2. For example, for a 96-well plate, there are 96 apertures 27 or holes that are formed in the base plate 25 for receiving the first ends of the optical fibers 24 with each aperture 27 or hole positioned so that it is substantially centered on the well 22 when the optically transparent AST plate 20 is placed in the slot or opening 18. The base plate 25 defines a bottom surface of the slot/opening 18 and when the optically transparent AST plate 20 is placed on top of the base plate 25 when loaded into the opto-mechanical attachment 12.

The second or opposing end of the optical fiber 24 is secured to a header 26 formed in the base plate 25 to form an output array of optical fibers 24 therein. The header 26 is used dramatically increase the density of optical signals generated from the wells 22. In particular, the output array of optical fibers 24 in the header 26 has a cross-sectional area $A_2$ (as seen in FIG. 2) that is at least ten times (i.e., 10×) less than the cross-sectional area $A_1$ of the input array of optical fibers 24 that are formed in the base plate 25 (the cross-sectional area $A_1$ may also be referred to as the cross-sectional area of the wells of the optically transparent plate). Another way of saying this is that the density of "virtual" wells that is created at the header 26 by the array of optical fibers 24 is at least ten times as large as the density of actual wells 22 in the optically transparent AST plate 20. Bending induced losses in each optical fiber 24 can create well-to-well signal variations, all of which can be calibrated out after the assembly of the fiber-optic array by using blank plates 20 and the normalization process described herein.

Still referring to FIGS. 1B and 1C, the opto-mechanical attachment 12 includes, in one embodiment, a lens 28 therein (e.g., a focal length of 45 mm although other focal lengths can be used). The location of the lens 28 is such that the lens 28 is interposed in an optical path formed between the array of optical fibers in the header 26 and the camera 102 of the portable electronic device 100. The lens 28 is secured in position in the upper half 12A of the opto-mechanical attachment 12. Thus, the light that exits the array of fibers 24 in the header 26 passes through the lens 28 prior to reaching the camera 102 of the portable electronic device 100. In some alternative embodiments, the lens 28 may be omitted entirely. For example, depending on the size of the attachment and the focal length of the camera 102, the lens 28 may be omitted entirely if the light emitted from the ends of the fibers in the heater 26 can be imaged with good resolution by the camera 102.

Still referring to FIGS. 1A-1C, a power source 30 is disposed on or in the opto-mechanical attachment 12. The power source 30 may include a number of batteries such as AAA batteries or the like or even power from the portable electronic device 100. The power source 30 can be switched on or off using a conventional switch or the like (not shown), or even a software-based switch operated using the software program or application 104. A low-noise, low dropout current regulator (not shown) may be included in the power circuit for the LEDs making up the illumination sources 16 to prevent power fluctuations and maintain constant illumination of the AST plate 20. Alternatively, the portable electronic device 100 may provide power to the opto-mechanical attachment through a cable or other connection. To maximize uniform illumination of the optically transparent AST plate 20 containing the wells 22, the individual light sources 26 may be centered against four (4) wells 22 as illustrated by position "X" in FIG. 3. Illumination from the light sources 26 is further homogenized using one or more diffusion layers 32 (in FIGS. 1B and 1C the diffusion layers are illustrated as only traversing part of the way over the optically transparent AST plate 20 for clarity but in the working embodiment they extend all the way across). The one or more diffusion layers 32 may include plastic diffuser sheets that have areas that cover substantially all of the optically transparent AST plate 20.

FIG. 4 illustrates the communication between the Smartphone application 104 on the portable electronic device 100 and the computing device 108 that is used for image analysis and data processing. As seen in FIG. 4, the computing device 108 may also be used for spatio-temporal tagging and storage of the results. For example, results may be stored in a database 109 that is accessible by the computing device 108 or a local storage device located in the computing device 108 (e.g., hard drive or memory). The database 109 or local storage device may also contain data related to calibration testing of control wells 22 in an optically transparent AST plate 20 using a normalization process explained in further detail below. The calibration testing of non-turbid wells 22 used for normalization may be performed by the manufacturer of the reader 10 and stored for later retrieval. The calibration testing may also be performed by the user or sell of the reader 10. Notably, this calibration needs to be done only a single time for a particular reader 10.

When a test is to be performed on a bacteria-containing sample, a test AST plate 20 is inserted into the opto-mechanical attachment 12. The wells 22 in the test AST plate 20 are pre-prepared or pre-loaded with the sample to be tested, liquid growth medium, along with dilutions of different antibiotics (e.g., two-fold dilutions). The AST plate 10 has been incubated for a sufficient number of hours to allow for bacteria reproduction to take place which in some embodiments is less than 24 hours. After inserting a new AST plate 20 into the reader 10, the AST plate 20 is illuminated with light from the light sources 16 and images are captured using the camera 102 of the portable electronic device 100 at three different exposure times (Dim: $1/1600$ sec, Medium: $1/1250$ sec, and Bright: $1/800$ sec) and saved as 10-bit DNG images. These 10-bit DNG images represent the best possible image quality obtainable on this mobile platform, with the other alternative being compressed JPEG format with 8-bit images (other file formats could also be used). With reference to the GUI 105 of the software or application 104 as seen in FIG. 3 and FIGS. 8A-8F, from the main menu, the user starts a new test analysis and first selects the three images previously captured to be used for processing (see FIG. 8B). Next, the user selects whether the plate type is Gram-negative or Gram-positive and then uses the search box to find the bacterium to-be-tested (FIG. 8C), such that the computing device 108 knows which wells 22 correspond to which drugs and how to analyze the MIC and perform automated drug susceptibility interpretation, respectively. The reader device 10, in one preferred embodiment, assumes that the user already knows the type or species of bacteria that is contained in the sample. This species of bacteria can then be selected by the user prior to analysis of the wells 22. With reference to FIG. 8C, by clicking the "submit" button, the images, plate type, and bacterium to-be-tested are sent to the computing device 108 for image processing and analysis.

Figure 5:
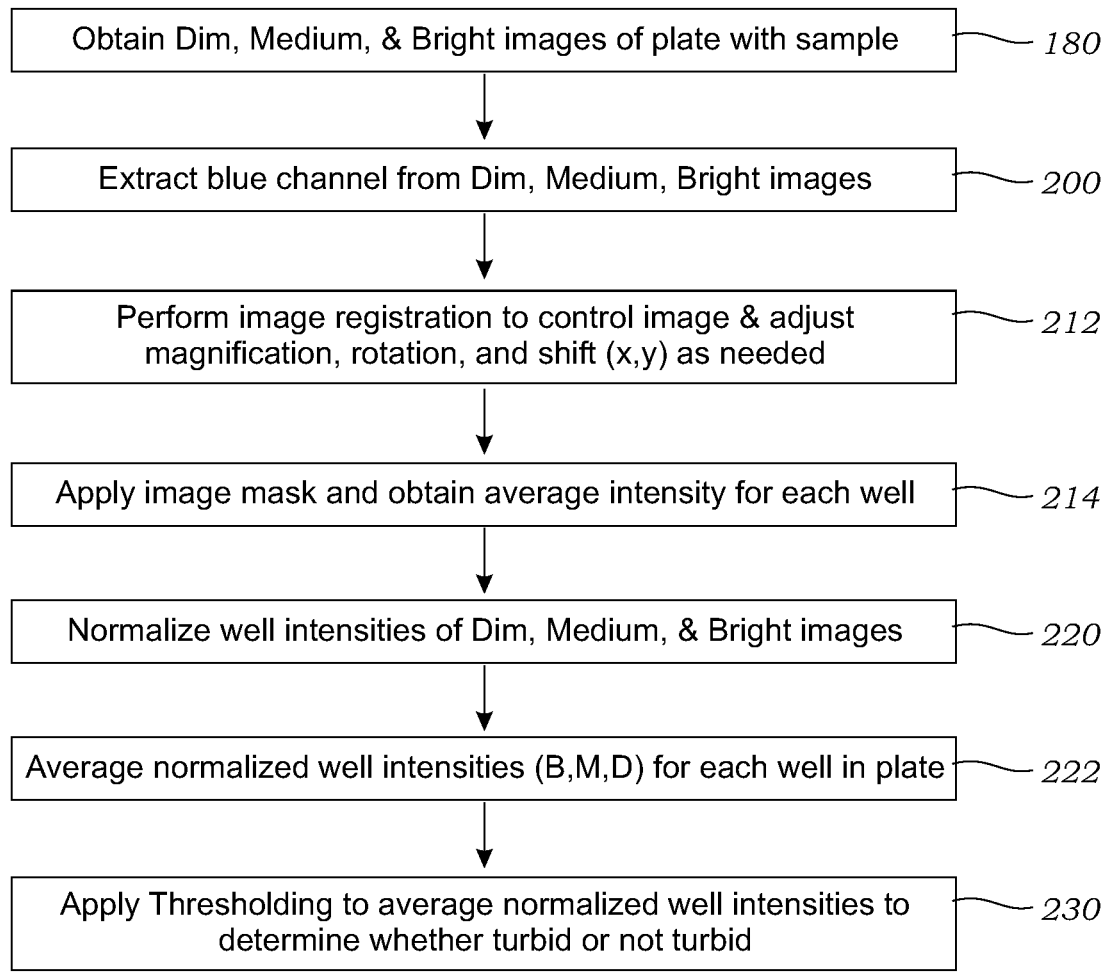
FIG. 5 illustrates a view of the sequence or flow of operations used to generate MIC values and susceptibility characterizations for drugs in the AST plate according to one embodiment.

With reference to FIG. 4, the operations performed in the computing device 108 first includes the extraction of the blue channel from the color images obtained from the camera 102 as seen in operation 200 of FIGS. 4 and 5 (other color channels could also be used). From the blue channel images for the dim, medium, and bright illumination conditions, the software 104 finds the locations of the wells 22 and extracts intensity values for each well 22 as seen in operation 210. The well intensities from the dim, medium, and bright illumination conditions are then subject to a normalization process (described in more detail below) as seen in operation 220. The normalized well intensities of the wells 22 of the AST plate 20 are then used to determine whether a particular well 22 of the AST plate 20 is turbid or not turbid. This operation is illustrated as operation 230 in FIG. 3. Next, as seen in operation 240, the turbidity of the wells 22 contained in the AST plate 20 is used to generate MIC values as well as susceptibility characterizations for the drugs that are used in the AST plate 20. MIC values are generated using the layout or map of the drugs and dilutions used in the AST plate 20. The lowest concentration of a particular drug within the panel that produces no turbidity is used to generate the MIC value. A map or table 114 is also used to correlate the MIC value generate a susceptibility characteristic for each drug in the panel. For example, these susceptibility classifications include susceptible, intermediate or indeterminate, and resistant. As seen in FIG. 4, the results (i.e., MIC values and susceptibility characteristics) for each drug in the panel are returned to the portable electronic device 100 for display to the user in the GUI 105.

FIG. 5 illustrates another view of the sequence or flow of operations used to generate MIC values and susceptibility characterizations for drugs in the AST plate 20. As seen in FIG. 5, in operation 180 the computing device 108 obtains the dim, medium, and bright images of the AST plate 20 containing the sample and panel of drugs. For the experiments described herein, the computing device 108 that received the images was a server. On receiving a new request, the computing device 108, which in the experiments described herein was implemented in Python using the Twisted framework, adds the request to the job queue and saves the images and job details to local storage, which may include a database 109 or a local storage device such as hard drive, solid state drive, or memory. Each DNG image is converted into 16-bit tagged image file format (TIFF) and the pixels corresponding to the blue channel are extracted from the raw Bayer image in operation 200. Subsequent processing of the blue channel images is performed using MATLAB® software 112 for image processing. The server 108 also has pre-recorded information of the mapping between the optical fibers 24 of the AST plate reader 10 and the individual wells 22 of a 96-well plate 20 (e.g., from control plates). This 2D mapping does not change from image to image, and only needs to be determined once for a given device design. To find this mapping function or template for calibration, a bright-field image (i.e., a control image) of a plate 20 is taken with deionized (DI) water with no turbidity in the wells 22 and the center of each optical fiber 24 is digitally calculated from this control image. The computing device 108 in operation 212 of FIG. 5 performs image registration to the control image and adjusts the magnification, rotation, and shift (x and y direction) as needed so that the wells 22 can be identified. To map successive images of the AST plates 20 to this control image, corner wells 22 are found using a threshold-based approach followed by morphological operations to separate adjacent wells 22. The corner wells 22 are then used to remove scaling and alignment issues that might be caused by the camera's auto-focus feature and potential misalignments between the camera 102 and fiber-optic array, where the known physical distances among the optical fibers 24 are exploited to find the center of each well 22. For example, to adjust for proper magnification, the distance between the two corner wells is known. If the observed distance in the test plate 20 between these same corner wells is too small or too large, the image may be adjusted to control for the different in magnification. Similarly, the image may be partially rotated (in the plane of the test plate 20) which can then be corrected by rotation of the same to align with the control image. Likewise, the image may need to be adjusted in the x or y directions (e.g., along the direction of rows or columns of the test plate 20).

Next, as seen in operation 214 of FIG. 5, a circular mask with a radius of twenty-five (25) pixels is then applied to reduce the interference from nearby optical fibers 24 before extracting the average intensity of each well's respective signal. After extracting each well's pixel intensity, the average intensities per well 22 for the dim, moderate, and bright images are each normalized, as seen in operation 220 (FIGS. 4 and 5), with respect to the average intensities of control images at each exposure time to scale the intensities from 0 to 1, with 1 representing complete transmittance of light through the well relative to the DI control. To maximize the dynamic range, the normalized transmittance values for each well from the dim, moderate, and bright images are first scaled and then averaged, as seen in operation to obtain a single higher dynamic range value for each well 22.

Figure 6:
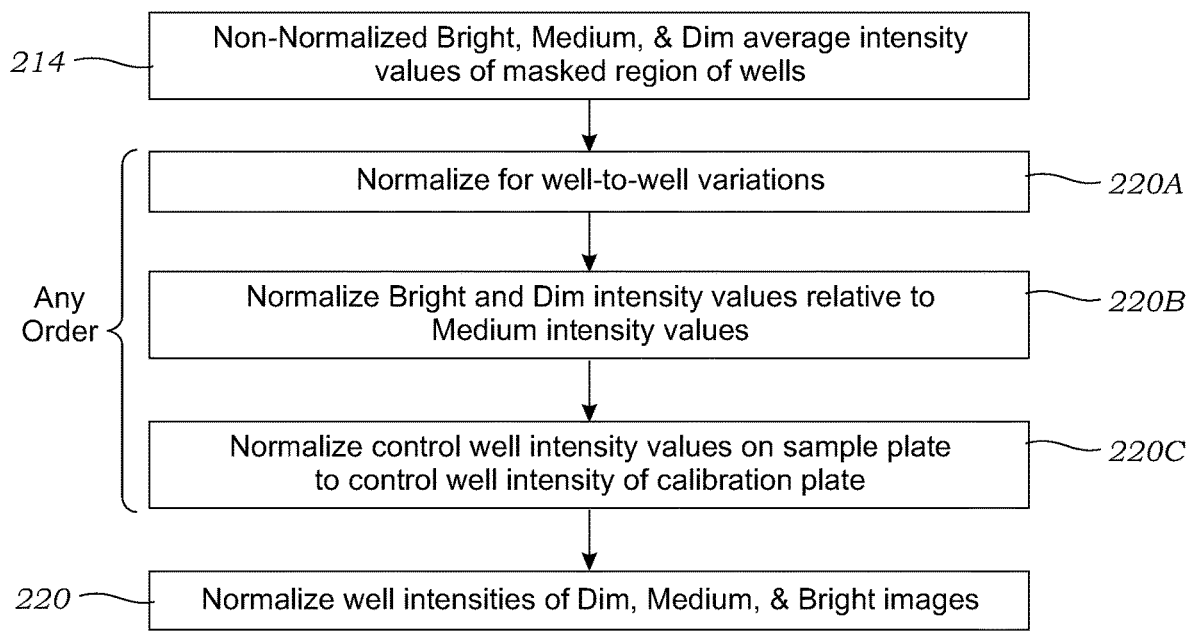
FIG. 6 illustrates a more detailed view of the operation of normalizing or scaling the well intensities of the wells from the dim, medium, and bright images.

FIG. 6 illustrates a more detailed view of the operation 220 of normalizing or scaling the well intensities of the wells 22 from the dim, medium, and bright images. As seen in operation 214 of FIG. 6, the non-normalized average intensity values of the circular masked regions (e.g., 25 pixel radius) are obtained for the bright, medium, and dim images. In operation 220A a first normalization factor is applied that normalizes for well-to-well variations using a control plate that contains non-turbid control solutions in each well. The control plate is imaged under the bright, medium, and dim conditions as explained herein. For example, certain wells 22 may be appear brighter than other wells 22 in the same AST plate 20 due fiber-to-fiber variations. This well-to-well variance may be normalized or compensated using a ratio of the measured well intensity to the maximum intensity for each well using the control plate (with blank controls). This will adjust for well-to-well variance. In operation 220B, a second normalization factor is applied that normalizes the bright and dim intensities relative to the medium intensity values again using the control plate containing the non-turbid wells that is imaged at the three exposures (i.e., bright, medium, dim). This variance based on illumination conditions may be normalized or compensated using a ratio of the maximum observed well at medium illumination conditions to the maximum observed well at dim and bright illumination conditions. Thus, dim results are upward adjusted relative to medium conditions while bright results are downward adjusted to medium conditions. In operation 220C, a third normalization factor is applied that adjusts or normalizes between control well intensities on the sample AST plate 20 (e.g., there are two such control wells 22 on the AST plate 20 in one embodiment) to control well intensities on a separate calibration plate, or in one embodiment, on a plurality of control plates. In this last normalization factor, small changes may be present between different non-turbid control wells. This last normalization factor is typically not that significant and, in some embodiments, could be omitted. These three factors are combined together (in a multiplication operation) to generate normalized intensity values for each well 22 in the AST plate 20 for the dim, medium, and bright image conditions. These values (dim, medium, and bright) are averaged as seen in operation 222 of FIG. 4 to generate a single, normalized and averaged intensity value for each well 22. It should be understood that the order of the various normalization operations may occur in different sequences.

To determine whether a particular well 22 contains sufficient turbidity or not, a threshold-based approach is used to determine the cut-off transmittance value for each well 22. As the turbidity increases, the light transmittance through the well decreases. This operation is illustrated as operation 230 in FIGS. 4 and 5. In particular, thresholding is applied to average normalized well intensities of sample-containing wells to determine whether a particular well 22 is classified as "turbid" or "not turbid." To choose an accurate threshold value for each well 22, the normalized transmittance values of wells 22 with no turbidity are extracted from a training set of blank reference plates 20 (i.e., plates with drugs but no microbes). For example, sixty (60) such plates that are blanks can be imaged to determine the mean transmittance at each well 22. This data may be stored in the database 109 or other local storage device. In one embodiment, from this set of normalized transmittance values from wells 22 with no turbidity, a threshold of two times the standard deviation below the mean of that particular well 22 is used to determine whether a given test or sample-containing well 22 is statistically likely to have microbial growth represented by turbidity. Those wells 22 that have an averaged, normalized intensity level that is lower than two times the standard deviation below the mean "not turbid" value are classified as "turbid" while wells 22 that don't meet that criteria are classified as "not turbid." Of course, other measures may be used for defining the cutoff or threshold. For example, fractional standard deviation may also be used for a cutoff or threshold. In addition, the threshold could also include a numerical cutoff of intensity or other multiple of the standard deviation.

Figure 3:
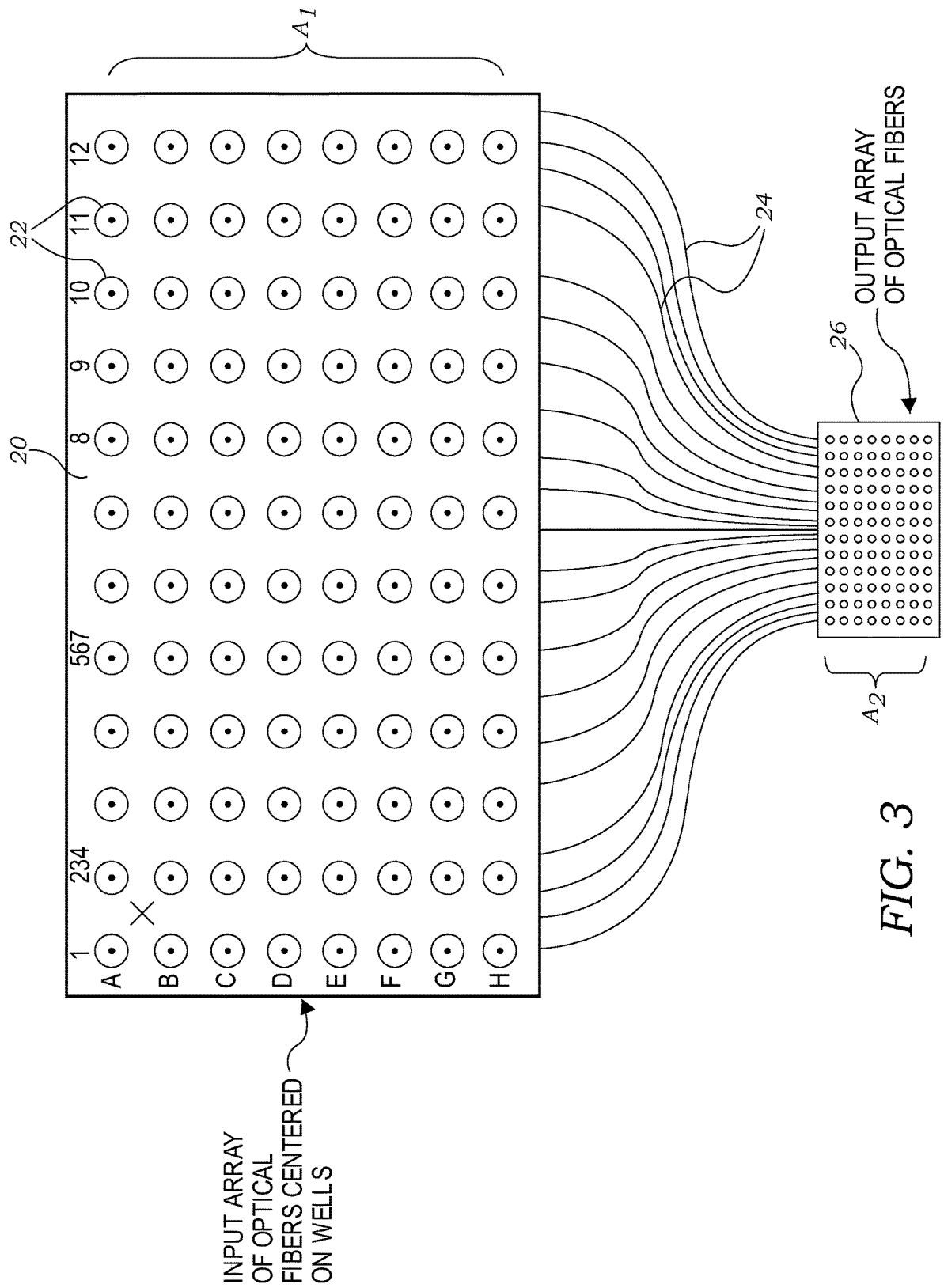
FIG. 3 illustrates a header used to hold optical fibers in the AST plate reader.
Figure 7:
FIG. 7 illustrates the layout of a map or table for the AST plate with susceptibility characterizations for each drug at different concentration levels.

With reference to FIG. 3, after the wells 22 are classified as "turbid" or "not turbid," the software 112 generates MIC values and susceptibility characterizations for the drug(s) on the AST plate 20. For a given type of AST plate 20 (i.e., Gram-negative or Gram-positive), the MIC value for each drug is determined by finding the lowest concentration of drug in a drug-specific set of wells 22 that contains no turbidity. More specifically, the MIC value is based on the adjacent, well 22 that is classified as not turbid as this well represents the lowest concentration of antibiotic that prevented bacterial growth (i.e. the MIC). Depending on the selected microbe of interest, drug susceptibility interpretations are automatically made by the software 112 based on the MIC for each drug. FIG. 7 illustrates the layout of a map or table 114 for the AST plate 20 with susceptibility characterizations for each drug at different concentration levels. The map or table 114 with susceptibility characterizations for each drug at different concentration levels may be stored in a database (e.g., database 109 or other local storage device) as a look-up table or the like. In some embodiments, the map or table 114 for each different bacterium may be stored in the database 109 or local storage device. For example, in looking at FIG. 7 with the example of the drug ampicillin (AM), various concentrations (μg/ml) of this drug is present within wells B1, C1, D1, E1 along with a growth medium. If wells B1 and C1 were classified as turbid while wells D1 and E1 were classified as not turbid, the MIC reading would be 16 μg/ml (e.g., looking at concentration in well D1). Likewise, the susceptibility characterization would be classified as "indeterminate" using the map or table 114.

As seen in FIG. 7, the map or table 114 includes standard drug concentrations populated in each well for a Gram-negative 96-well microtiter plate at the UCLA Medical Center and is coded (e.g., color coded although other classifications schemes can be used) with interpretive criteria readings for *Klebsiella pneumoniae*. One susceptibility characterization is "susceptible," another is "intermediate," another is "susceptible dose dependent" or (SDD) (a newer classification which means that a higher dosage of drug may be needed for treatment), and still another is "resistant." The minimum inhibitory concentration (MIC) of each drug for the tested bacteria species is determined by reading the first well in each drug series that contains no visible microbial growth, represented by well turbidity. The susceptibility of the microbial to each drug is determined based on the MIC as per the coded map or table 114. That is to say, once the particular well 22 is identified as the MIC well 22 (based on the minimum concentration that inhibited microbial growth) one can then automatically determine the interpretive characterization of the sample using the map or table 114. Table 1 below illustrates the list of drugs and drug combinations prepared for the Gram-negative AST plate 20 along with the common abbreviations that were used with the software application run on the portable electronic device 100 according to one embodiment.

TABLE 1

| Abbreviation | Drug Name |
|---|---|
| AM | Ampicillin |
| A/S | Ampicillin-Sulbactam |
| TMP/SMX | Trimethoprim-sulfamethoxazole |
| CPM | Cefepime |
| MPM | Meropenem |
| GM | Gentamicin |
| ETP | Ertapenem |
| TB | Tobramycin |
| AK | Amikacin |
| CZ | Cefazolin |
| CTRX | Ceftriaxone |
| CAZ/AVI | Ceftazidime-Avibactam |
| CAZ | Ceftazidime |
| PIP/TAZ | Pipercillin-tazobactam |
| IPM | Imipenem |
| CIP | Ciprofloxacin |
| LVX | Levofloxacin |

After the turbidity decisions of the wells 22, the MIC determination, and the drug susceptibility characterization are all automatically made using the software 112, the results are stored in a database 109 on or associated with the computing device 108, and are also transmitted or returned back to the originating portable electronic device 100. Typically, the results are returned to the portable electronic device 100 within about within one (1) minute. Execution time is thus quick. According to one embodiment, on the Smartphone application 104, the user can review the results via the history page (see FIG. 8D), which lists all the uploaded tests and the microbes tested for. After clicking on a test, the user can view the susceptibility results in a scrollable table (see FIG. 8E), with the drug or drug combination in the first column, the MIC in the second column, and the susceptibility interpretation in the third column (other orders or visual presentation schemes may also be used). The user can also swipe the page to see the detection of well turbidity in a color-coded table format (see FIG. 8F), with, for example, rectangles indicating no turbidity and ovals indicating the wells that contain turbidity.

Experimental

Design of Clinical Testing

The AST plate reader 10 described herein was tested using Klebsiella pneumonia isolates from patient samples collected by the UCLA hospital system and prepared and tested at the UCLA Clinical Microbiology Laboratory. Antimicrobial agents were tested using two-fold serial dilutions and the concentration range varies with the drug, the organism tested, and the site of the infection. For the microdilution method, the antimicrobial dilutions are in 0.1 mL volumes that are contained in wells of a 96 well microdilution tray. The drug panels are then stored frozen until they are inoculated. Briefly, a suspension of the tested organism is prepared in sterile saline to a 0.5 McFarland standard using isolated colonies. 1.5 mL of the suspension is transferred to an inoculating tray containing 40 mL of sterile distilled water. The inoculating tray has prongs that allow for transfer of bacteria into each well of the 96 well drug plate. The plate is then incubated for 24 hours at 37° C. The panels are quality controlled with the appropriate ATCC (American Type Culture Collection) organisms. The bacterial pathogen identification was performed after the culture of the organism by MALDI-TOF (matrix assisted laser desorption/ionization-time of flight) identification method. For each plate, an expert diagnostician inspected the plate and recorded the presence or absence of turbidity in each well, which was used as a gold standard. Each plate was then imaged using the AST plate reader 10 secured to a portable electronic device 100 in the form of a mobile phone (Nokia Lumia 1020). Experiments were conducted at the UCLA Clinical Microbiology Laboratory by medical personnel trained on how to use the AST plate reader 10.

The MIC and drug susceptibility for *Klebsiella pneumoniae* were determined using the map or table 114 of FIG. 6. For each drug, the MIC value was determined by finding the well that contained the lowest concentration of drug that was classified as "not turbid." The susceptibility characterization was determined using a look-up table that was stored and retrieved by the server.

Results

The capability of the mobile phone-based AST plate reader 10 to perform highly accurate MIC determination and drug susceptibility interpretation, greatly exceeding the FDA-defined criteria for susceptibility testing, with clinical isolates of the Gram-negative bacterium *Klebsiella pneumoniae*. Table 2 below shows the mean and standard deviation for well turbidity detection accuracy, well turbidity detection sensitivity, well turbidity detection specificity, MIC determination accuracy, and drug susceptibility interpretation accuracy of the AST plate reader 10 when using only the best performing single exposure image (i.e., bright exposure) and when combining the dim, moderate, and bright exposure images to digitally increase the dynamic range. In these trials, thirty-nine (39) randomly chosen patient isolate plates and twenty-one (21) blank plates without microbial content were used to determine an optimal threshold for well turbidity detection, followed by a blind-test on the remaining thirty-nine (39) patient isolate plates, none of which were used in the training.

TABLE 2

| Images used | Well Accuracy | Well Sensitivity | Well Specificity | MIC Accuracy | Drug Susceptibility Accuracy | Very Major Error Percentage | Major Error Percentage | Minor Error Percentage |
|---|---|---|---|---|---|---|---|---|
| (a) Single exposure (1/800) | 96.94% ± 1.30% | 98.83% ± 0.70% | 96.24% ± 1.92% | 94.89% ± 1.14% | 98.55% ± 0.58% | 0.43% ± 0.68% | 0.17% ± 0.13% | 1.23% ± 0.54% |
| (b) Combination of three exposures (1/1600, 1/1250, 1/800) | 98.21% ± 0.29% | 98.56% ± 0.37% | 98.08% ± 0.37% | 95.12% ± 0.87% | 99.23% ± 0.23% | 0% ± 0% | 0.16% ± 0.18% | 0.65% ± 0.20% |

Blank plates were included in the training set since some wells always exhibit bacterial growth due to high antimicrobial resistance. This training and blind-testing process was performed fifty (50) times with random sampling of patient plates to generate the standard deviations. As can be seen from Table 2, combining multiple image exposures significantly increases the overall accuracy of AST using the reader 10 and reduces variability for well turbidity detection, with significant improvements for MIC determination and drug susceptibility interpretation. Based on these results, an average well turbidity detection accuracy of 98.21% was achieved, a minimum inhibitory concentration accuracy of 95.12%, and a drug susceptibility interpretation accuracy of 99.23%, with no very major errors (i.e., resistant misdiagnosed as susceptible), 0.16% major errors (i.e., susceptible misdiagnosed as resistant), and 0.65% minor errors (i.e., indeterminate/susceptible dose dependent-related misdiagnoses). To provide a reference for these numbers, the total ground truth dataset across seventy-eight (78) patient plates contains 960 susceptible decisions, 288 resistant decisions, 70 indeterminate decisions, and 8 susceptible dose dependent decisions.

To better explore potential drug susceptibility misdiagnoses using the mobile phone-based AST plate reader 10, Table 3 below shows the specific results for one training/test set of the multiple exposure results used in the statistical average reported in Table 3.

TABLE 3

| System Performance | |
| --- | --- |
| Well Accuracy | 98.25% |
| Well Sensitivity | 98.27% |
| Well Specificity | 98.23% |
| MIC Accuracy | 95.32% |
| Drug Susceptibility Accuracy | 99.55% |
| Very Major Error Percentage | 0% |
| Major Error Percentage | 0.21% |
| Minor Error Percentage | 0.30% |

Table 4 below illustrates drug susceptibility misdiagnoses using the AST reader 10. There are no very major errors (i.e., no resistant bacteria misdiagnosed as susceptible) and only one (1) major error (i.e., ~0.2% susceptible bacteria misdiagnosed as resistant) and two (2) minor errors (i.e., ~0.3% indeterminate/susceptible dose dependent-related misdiagnoses) out of a total of 663 MIC and drug susceptibility interpretations across thirty-nine (39) patient test plates, with no error occurring twice on the same plate or for the same drug, exceeding the FDA criteria for clinical susceptibility testing. The three specific drug susceptibility misdiagnoses (plates 1, 5 and 8) are all low-risk misdiagnoses (i.e., one major error and two minor errors but no very major errors).

TABLE 4

| Drug Susceptibility Misdiagnoses | | | | |
| --- | --- | --- | --- | --- |
| Plate ID | Drug | Automated System Decision | Diagnostician Decision | Error Type |
| 1 | AM | Resistant | Indeterminate | Minor |
| 5 | A/S | Resistant | Indeterminate | Minor |
| 8 | MPM | Resistant | Susceptible | Major |

Due to the design of the Gram-negative MTP used by UCLA Clinical Microbiology Laboratory (FIG. 7), only ninety-five (95) wells are used per plate, with one (1) well used as a positive control, (1) well used as a positive dye, and the remaining ninety-three (93) wells used for drug testing, which provides for a total of 3705 turbidity-assessable wells across 39 patient isolate test plates used in the blind testing. These wells are used to test seventeen (17) drugs and drug combinations per MTP (Table 1) for a total of 663 MIC determinations and drug susceptibility interpretations.

Discussion

A cost-effective portable AST reader system has been demonstrated that includes a mobile phone and a 3D-printed opto-mechanical reader attachment that can replace an expert diagnostician with a lab technician trained in the usage of the reader device for interpreting 96-well microtiter plates for antimicrobial susceptibility testing. The mobile platform achieved 95.12% MIC determination accuracy and 99.23% drug susceptibility interpretation accuracy for *Klebsiella pneumonia* susceptibility testing, exceeding the FDA criteria for performing AST analysis. Since well turbidity presents similar optical characteristics, adding the ability to test other plate types and microbes can be as simple as updating the server logic with the drug series information and drug-microbe susceptibility interpretation (e.g., map or table of FIG. 7), allowing this platform to easily scale to test other bacteria.

The AST reader is especially useful in resource-limited settings given its ability to remove the need for a trained diagnostician, enabling local technicians to easily be able to conduct high-throughput antimicrobial susceptibility testing. In fact, clinical microbiology is rapidly progressing toward automation. Multiple platforms are now available for automated organism identification including smart incubators and MALDI-TOF based proteomic identification. This AST reader system fits very well with future clinical microbiology diagnostic labs, where the gold standard for AST testing and broth microdilution can be automated for turbidity reading, MIC interpretation, and appropriate antibiotic prescription. Furthermore, paired with the Smartphone's wireless connectivity and inherent digital record-saving, this platform can enable widespread and easy collection of drug resistance profiles for spatio-temporal tracking (using GPS and time stamps which are stored along with the images obtained with the reader 10), which could be especially useful for isolating and eliminating drug resistant strains of harmful bacteria. An additional advantage of this technology is the possibility of examining turbidity or bacterial growth in the presence of a drug at an earlier time point than is currently read (i.e., 24 hours). Optical analysis by the digital reader may potentially reveal early turbidity and allow for a more rapid turn-around time of the AST results to the physician.

While embodiments of the present invention have been shown and described, various modifications may be made without departing from the scope of the present invention. The invention, therefore, should not be limited, except to the following claims, and their equivalents.

What is claimed is:

1. A method of performing antimicrobial susceptibility testing (AST) on a bacteria-containing sample using an opto-mechanical reader device configured to mount on a portable electronic device having a camera comprising:
   securing the opto-mechanical reader device to the portable electronic device, the opto-mechanical reader device comprising:
   a housing including a plurality of illumination sources;
   a slot or opening dimensioned to receive an optically transparent plate having an array of wells;

a base plate disposed within the housing and defining a bottom surface of the slot or opening that receives the optically transparent plate;

a plurality of optical fibers having first ends secured to the base plate and arranged in an input array having a first cross-sectional area and second ends mounted to a header and arranged in an output array having a second cross-sectional area that is at least ten times less than the first cross-sectional area, each fiber arranged to transmit light from one of the wells to the camera to generate one or more images, wherein the housing comprises an optical window or second opening disposed with respect to the camera to receive light from the output array;

loading the optically transparent plate having an array of wells containing the bacteria-containing sample, growth medium, and a panel of drugs of differing concentrations into the opto-mechanical reader device;

illuminating the wells in the optically transparent plate using the plurality of illumination sources contained in the opto-mechanical reader device;

acquiring one or more images of the wells in the array with the camera of the portable electronic device, wherein the one or more images represent light transmittance through the wells in the array;

transferring the one or more images to image processing software;

processing the one or more acquired images with image processing software executed by at least one processor to classify each well as turbid or not turbid based on a transmittance threshold assigned to each particular well in the array of wells and which constitutes a turbidity classification and generating MIC values and a susceptibility characterization for each drug in the panel based on the turbidity classification of the array of wells; and displaying MIC values and the susceptibility characterizations for each drug in the panel on the portable electronic device or other computing device.

2. The method of claim 1, further comprising transmitting the one or more images to a separate computing device, wherein the separate computing device comprises the at least one processor and the imaging processing software and wherein the separate computing device returns the MIC values and the susceptibility characterizations for each drug in the panel to the portable electronic device.

3. The method of claim 2, wherein the separate computing device comprises one of a local computer, a remote computer, tablet PC, personal computer, Smartphone, or a mobile computing device.

4. The method of claim 2, wherein the one or more transmitted images comprises a plurality of images captured at a plurality of different camera exposure times obtained using the camera.

5. The method of claim 4, wherein the image processing software generates normalized light transmittance values for each well based on the images of the wells obtained at the plurality of different camera exposure times and subjecting the normalized light transmittance values of each well to a threshold comparison using the image processing software.

6. The method of claim 5, wherein the threshold is established at a normalized light transmittance value level that corresponds to about two times the standard deviation below the average value of the normalized light transmittance value of a blank reference plate well with no turbidity.

7. The method of claim 1, wherein the MIC values and susceptibility characterizations are displayed on a graphical user interface of a software program or application running on the portable electronic device.

8. The method of claim 2, wherein MIC values and susceptibility characterizations are returned to the portable electronic device within about one (1) minute or less after transmission to the separate computing device.

9. The method of claim 1, wherein an accuracy of well turbidity detection is 98%.

10. The method of claim 1, wherein MIC values have an accuracy of 98%.

11. The method of claim 1, wherein an accuracy of susceptibility characterizations is 98%.

12. A method of performing antimicrobial susceptibility testing (AST) on a bacteria-containing sample using an opto-mechanical reader device configured to mount on a mobile phone having a camera comprising:

securing the opto-mechanical reader device to the mobile phone, the opto-mechanical reader device comprising:
a housing including an array of illumination sources;
a slot or opening dimensioned to receive an optically transparent plate having an array of wells;
a base plate disposed within the housing and defining a bottom surface of the slot or opening that receives the optically transparent plate;
a plurality of optical fibers having first ends secured to the base plate and arranged in an input array having a first cross-sectional area and second ends mounted to a header and arranged in an output array having a second cross-sectional area that is at least ten times less than the first cross-sectional area, each fiber arranged to transmit light from one of the wells to the camera to generate a plurality of images, wherein the housing comprises an optical window or second opening disposed with respect to the camera to receive light from the output array;

loading the optically transparent plate having an array of wells containing the bacteria-containing sample, growth medium, and a panel of drugs of differing concentrations into the opto-mechanical reader device;

illuminating the wells in the optically transparent plate using the array of illumination sources;

acquiring a plurality of images of the wells with the camera of the mobile phone, wherein the plurality of images represent light transmittance through the wells captured by the camera at different camera exposure times;

transmitting the plurality of images to a separate computing device;

processing the plurality of transmitted images with image processing software executed by at least one processor in the separate computing device to generate normalized light transmittance values for each well based on the plurality of images of the wells obtained at the plurality of different camera exposure times and classify each well as turbid or not turbid based on a transmittance threshold assigned to each particular well in the array of wells and which constitutes a turbidity classification and generating MIC values and a susceptibility characterization for each drug in the panel based on the turbidity classification of the array of wells; and transmitting the MIC values and the susceptibility characterizations for each drug in the panel from the separate computing device to the mobile phone or another computing device for display thereon.

13. A method of performing antimicrobial susceptibility testing (AST) on a bacteria-containing sample using an opto-mechanical reader device configured to mount on a mobile phone comprising:
securing the opto-mechanical reader device to the mobile phone, the opto-mechanical reader device comprising:
a housing including an array illumination sources;
a slot or opening dimensioned to receive an optically transparent plate having an array of wells;
a base plate disposed within the housing and defining a bottom surface of the slot or opening that receives the optically transparent plate;
a plurality of optical fibers having first ends secured to the base plate and arranged in an input array having a first cross-sectional area and second ends mounted to a header and arranged in an output array having a second cross-sectional area that is at least ten times less than the first cross-sectional area, each fiber arranged to transmit light from one of the wells to the camera to generate a plurality of images, wherein the housing comprises an optical window or second opening disposed with respect to the camera to receive light from the output array;
loading into the opto-mechanical reader device the optically transparent plate having an array of wells containing the bacteria-containing sample, growth medium, and a panel of drugs of differing concentrations;
illuminating the wells in the optically transparent plate using an array of illumination sources contained in the opto-mechanical reader device;
acquiring a plurality of images of the wells with the camera of the mobile phone, wherein the plurality of images represent light transmittance through the wells captured by the camera at different camera exposure times;
processing the plurality of transmitted images in the mobile phone to generate normalized light transmittance values for each well based on the plurality of images of the wells obtained at the plurality of different camera exposure times and classify each well as turbid or not turbid based on a transmittance threshold assigned to each particular well in the array of wells and which constitutes a turbidity classification and generating MIC values and a susceptibility characterization for each drug in the panel based on the turbidity classification of the array of wells; and
displaying MIC values and the susceptibility characterizations for each drug in the panel on the mobile phone.

14. A system for performing antimicrobial susceptibility testing (AST) on a bacteria-containing sample comprising:
a portable electronic device having a camera;
an optically transparent plate having an array of wells containing the bacteria-containing sample, growth medium, and a panel of drugs of differing concentrations into the opto-mechanical reader device;
an opto-mechanical reader device configured to mount on the portable electronic device and including a housing having a slot or opening and a base plate defining a bottom surface of the slot or opening that receives the optically transparent plate, the opto-mechanical reader device having a plurality of illumination sources contained in the opto-mechanical reader device and configured to illuminate the array of wells, the opto-mechanical reader device further comprising a plurality of optical fibers having first ends secured to the base plate and arranged in an input array having a first cross-sectional area and second ends mounted to a header and arranged in an output array having a second cross-sectional area that is at least ten times less than the first cross-sectional area, each fiber arranged to transmit light from one of the wells to the camera to generate one or more images, wherein the housing comprises an optical window or second opening disposed with respect to the camera to receive light from the output array; and
image processing software contained in the portable electronic device that is executable by at least one processor to process the one or more images and classify each well as turbid or not turbid based on a transmittance threshold assigned to each particular well in the array of wells and which constitutes a turbidity classification and generating MIC values and a susceptibility characterization for each drug in the panel based on the turbidity classification of the array of wells.

15. The system of claim 14, wherein the portable electronic device comprises one of a mobile phone, tablet PC, webcam, and digital camera.

16. The system of claim 14, wherein the generated MIC values and susceptibility characterizations are displayed on a display on the portable electronic device.

17. The system of claim 14, further comprising a database or local storage device associated with or in communication with the portable electronic device.

18. The method of claim 5, wherein the plurality of different exposure times comprises three different camera exposure times.

19. The method of claim 12, wherein the plurality of different exposure times comprises three different camera exposure times.

20. The method of claim 13, wherein the plurality of different exposure times comprises three different exposure times.

* * * * *